United States Patent
Kim et al.

(10) Patent No.: US 9,725,389 B2
(45) Date of Patent: *Aug. 8, 2017

(54) MONOMER FOR A HARDMASK COMPOSITION, HARDMASK COMPOSITION COMPRISING THE MONOMER, AND METHOD FOR FORMING A PATTERN USING THE HARDMASK COMPOSITION

(71) Applicant: CHEIL INDUSTRIES INC., Gyeongsangbuk-do (KR)

(72) Inventors: Yun-Jun Kim, Uiwang-si (KR); Hwan-Sung Cheon, Uiwang-si (KR); Youn-Jin Cho, Uiwang-si (KR); Yong-Woon Yoon, Uiwang-si (KR); Chung-Heon Lee, Uiwang-si (KR); Hyo-Young Kwon, Uiwang-si (KR); Yoo-Jeong Choi, Uiwang-si (KR)

(73) Assignee: Cheil Industries, Inc., Gumi-Si, Gyeongsangbuk-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/364,829

(22) PCT Filed: Nov. 29, 2012

(86) PCT No.: PCT/KR2012/010203
§ 371 (c)(1),
(2) Date: Jun. 12, 2014

(87) PCT Pub. No.: WO2013/100409
PCT Pub. Date: Jul. 4, 2013

(65) Prior Publication Data
US 2014/0342273 A1 Nov. 20, 2014

(30) Foreign Application Priority Data
Dec. 30, 2011 (KR) .......... 10-2011-0147384
Dec. 30, 2011 (KR) .......... 10-2011-0147860

(51) Int. Cl.
C07C 39/21 (2006.01)
C07C 39/205 (2006.01)
C07C 33/26 (2006.01)
G03F 7/039 (2006.01)
G03F 7/11 (2006.01)
H01L 21/027 (2006.01)
C07C 39/225 (2006.01)
G03F 1/00 (2012.01)
G03F 7/09 (2006.01)
G03F 7/20 (2006.01)
H01L 21/02 (2006.01)
H01L 21/033 (2006.01)
H01L 21/311 (2006.01)

(52) U.S. Cl.
CPC ............ *C07C 39/21* (2013.01); *C07C 39/225* (2013.01); *G03F 1/00* (2013.01); *G03F 7/094* (2013.01); *G03F 7/20* (2013.01); *H01L 21/02118* (2013.01); *H01L 21/02282* (2013.01); *H01L 21/0332* (2013.01); *H01L 21/31144* (2013.01)

(58) Field of Classification Search
None
See application file for complete search history.

(56) References Cited

U.S. PATENT DOCUMENTS

| | | | | |
|---|---|---|---|---|
| 6,423,462 B1 * | 7/2002 | Kunita | .................. | B41C 1/1016 430/156 |
| 6,576,562 B2 * | 6/2003 | Ohuchi | ............... | H01L 21/0271 257/E21.024 |
| 7,862,990 B2 | 1/2011 | Yoon et al. | | |
| 8,637,219 B2 * | 1/2014 | Cho et al. | .................. | 430/270.1 |
| 9,018,776 B2 * | 4/2015 | Song et al. | .................... | 257/786 |
| 9,158,201 B2 * | 10/2015 | Lee | ............................ | G03F 7/26 |
| 9,244,351 B2 * | 1/2016 | Lee | ..................... | H01L 21/0276 |
| 2008/0305441 A1 * | 12/2008 | Yoon et al. | .................... | 430/323 |
| 2009/0176165 A1 * | 7/2009 | Cheon | ..................... | G03F 7/091 430/5 |
| 2010/0021830 A1 * | 1/2010 | Kim et al. | ........................ | 430/5 |

(Continued)

FOREIGN PATENT DOCUMENTS

CN 102115426 A 7/2011
CN 201566281 A 7/2012

(Continued)

OTHER PUBLICATIONS

Kito et al. "Precursors in the alkylation of 2-naphthol with benzyl alcohol in the presence of a base", J. Org. Chem., vol. 50(23) pp. 4628-4630(1985).*
International Search Report dated Feb. 25, 2013 in corresponding International Patent Application No. PCT/KR2012/010203.
Search Report dated Mar. 13, 2015 in corresponding Taiwanese Patent Application No. 101150569.
Taketoshi Kito, et al., "Precursors in the Alkylation of 2-Naphthol with Benzyl Alcohol in the Presence of a Base", The Journal of Organic Chemistry, vol. 50, Issue 3, p. 4628-4630, Nov. 1985.

(Continued)

*Primary Examiner* — Martin Angebranndt
(74) *Attorney, Agent, or Firm* — Lee & Morse, P.C.

(57) ABSTRACT

Disclosed are a monomer for a hardmask composition represented by the following Chemical Formula 1, a hardmask composition including the monomer, and a method of forming a pattern using the same.

[Chemical Formula 1]

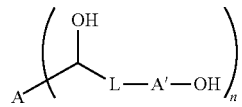

In Chemical Formula 1, A, A', L and n are the same as in the detailed description.

12 Claims, No Drawings

(56) References Cited

U.S. PATENT DOCUMENTS

| | | | | |
|---|---|---|---|---|
| 2010/0292175 | A1* | 11/2010 | Wessjohann et al. | 514/23 |
| 2010/0316949 | A1* | 12/2010 | Rahman | C08G 61/02 430/270.1 |
| 2011/0155944 | A1* | 6/2011 | Cho et al. | 252/62.51 R |
| 2012/0153511 | A1* | 6/2012 | Song et al. | 257/786 |
| 2012/0168894 | A1* | 7/2012 | Kim et al. | 257/499 |
| 2014/0186775 | A1* | 7/2014 | Lee et al. | 430/323 |
| 2014/0186777 | A1* | 7/2014 | Lee et al. | 430/325 |
| 2014/0335447 | A1* | 11/2014 | Lee et al. | 430/5 |
| 2015/0001178 | A1* | 1/2015 | Song et al. | 216/47 |
| 2015/0004531 | A1* | 1/2015 | Choi et al. | 430/5 |
| 2015/0187566 | A1* | 7/2015 | Park | H01L 21/0276 257/499 |
| 2015/0274622 | A1* | 10/2015 | Kim | C07C 39/14 216/49 |
| 2016/0005625 | A1* | 1/2016 | Shin | H01L 21/47 438/703 |
| 2016/0011511 | A1* | 1/2016 | Shin | H01L 21/47 430/323 |

FOREIGN PATENT DOCUMENTS

| | | |
|---|---|---|
| CN | 103959170 A | 7/2014 |
| JP | 62-252734 A | 11/1987 |
| JP | 05-113663 * | 5/1993 |
| JP | 06-145307 * | 5/1994 |
| JP | 06-219973 A | 8/1994 |
| JP | 08-339079 * | 12/1996 |
| JP | 2001-098358 A | 4/2001 |
| JP | 2004-158709 A | 6/2004 |
| JP | 2010524224 A | 7/2010 |
| JP | 2010529499 A | 8/2010 |
| JP | 2011144170 | 7/2011 |
| KR | 10-2008-0107210 A | 12/2008 |
| KR | 10-2009-0068444 A | 6/2009 |
| KR | 10-2009-0120827 A | 11/2009 |
| KR | 10-2011-0053136 A | 5/2011 |
| KR | 10-2011-0079201 A | 7/2011 |
| KR | 10-2013-0078432 A | 7/2013 |
| KR | 10-2013-0078745 A | 7/2013 |
| TW | 201018712 A1 | 5/2010 |
| TW | 201030470 A1 | 8/2010 |
| TW | 201134799 A1 | 10/2011 |
| TW | 201337468 A | 9/2013 |
| WO | WO-2010-041626 A1 | 4/2010 |

OTHER PUBLICATIONS

Search Report dated Oct. 20, 2015 in corresponding Taiwanese Patent Application No. 101150569.
Chinese Office Action dated Oct. 26, 2016.

* cited by examiner

MONOMER FOR A HARDMASK COMPOSITION, HARDMASK COMPOSITION COMPRISING THE MONOMER, AND METHOD FOR FORMING A PATTERN USING THE HARDMASK COMPOSITION

BACKGROUND OF THE INVENTION (a) Field of the Invention

A monomer for a hardmask composition, a hardmask composition including the monomer, and a method of forming a pattern using the hardmask composition are disclosed.

(b) Description of the Related Art

Recently, the semiconductor industry has developed to an ultra-fine technique having a pattern of several to several tens nanometer size. Such ultra-fine technique essentially needs effective lithographic techniques. The typical lithographic technique includes providing a material layer on a semiconductor substrate; coating a photoresist layer thereon; exposing and developing the same to provide a photoresist pattern; and etching the material layer using the photoresist pattern as a mask.

Nowadays, according to small-sizing the pattern to be formed, it is difficult to provide a fine pattern having an excellent profile by only above-mentioned typical lithographic technique. Accordingly, a layer, called a hardmask layer, may be formed between the material layer and the photoresist layer to provide a fine pattern.

The hardmask layer plays a role of an intermediate layer for transferring the fine pattern of photoresist to the material layer through the selective etching process. Accordingly, the hardmask layer requires to have characteristics such as chemical resistance, heat resistance, and etch resistance or the like to be tolerated during the multiple etching processes.

On the other hand, it has been recently suggested to form a hardmask layer by a spin-on coating method instead of the chemical vapor deposition. The spin-on coating method may use the hardmask composition having dissolubility for a solvent.

However, the dissolubility and the characteristics required for the hardmask layer have the relationship against to each other, so a hardmask composition satisfying both is needed.

In addition, according to widening the application range of hardmask layer, the hardmask layer may be formed on a predetermined pattern by the spin-on coating method. In this case, the gap-fill characteristics of filling the hardmask composition in gap between patterns and the planarization characteristics are also required.

SUMMARY OF THE INVENTION

One embodiment provides a monomer for a hardmask composition that satisfies chemical resistance, heat resistance and etch resistance while ensures dissolubility for a solvent, gap-fill characteristics, and planarization characteristics.

Another embodiment provides a hardmask composition including the monomer.

Yet another embodiment provides a method of forming a pattern using the hardmask composition.

According to one embodiment, a monomer for a hardmask composition represented by the following Chemical Formula 1 is provided.

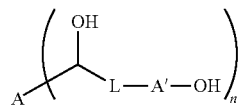

[Chemical Formula 1]

In Chemical Formula 1,

A, and A' are the same or different and are a substituted or unsubstituted aromatic group, L is a single bond or a substituted or unsubstituted C1 to C6 alkylene group, and n is an integer ranging from 1 to 5.

The aromatic group may include at least one selected from the following Group 1.

[Group 1]

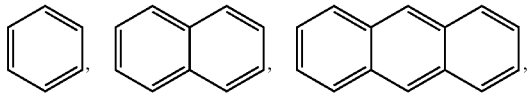

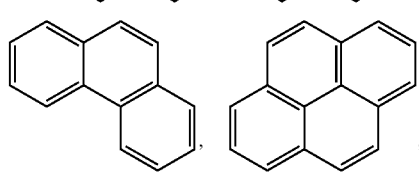

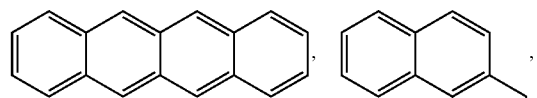

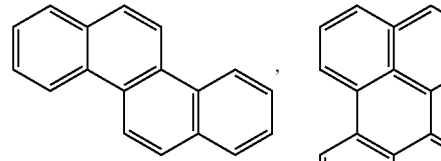

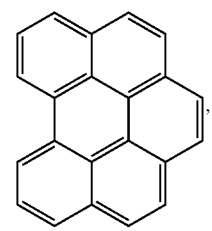

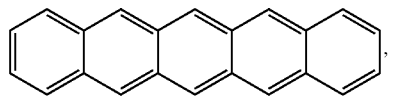

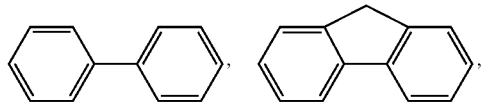

-continued

At least one of A and A' may include a substituted or unsubstituted polycyclic aromatic group.

The monomer for a hardmask composition may be, for example represented by the following Chemical Formula 1a, 1b, or 1c.

[Chemical Formula 1a]

[Chemical Formula 1b]

[Chemical Formula 1c]

In Chemical Formula 1a, 1b, or 1c, $A^1$ to $A^4$ are each independently a substituted or unsubstituted benzene group, a naphthalene group, a pyrene group, a perylene group, a benzoperylene group, a coronene group, or a combination thereof.

$L^1$ to $L^3$ are each independently a single bond or a substituted or unsubstituted C1 to C6 alkylene group.

The monomer may be, for example represented by the following Chemical Formula 1aa, 1bb, 1cc, 1dd, or 1ee.

[Chemical Formula 1aa]

[Chemical Formula 1bb]

[Chemical Formula 1cc]

[Chemical Formula 1dd]

[Chemical Formula 1ee]

The monomer may have a molecular weight of about 200 to 3,000.

According to another embodiment, a hardmask composition including the monomer and a solvent is provided.

The monomer may be included in an amount of about 0.1 to 30 w/t % based on the total amount of the hardmask composition.

According to yet another embodiment, provided is a method of forming a pattern that includes providing a material layer on a substrate, applying the hardmask composition on the material layer, heat-treating the hardmask composition to provide a hardmask layer, forming a silicon-containing thin layer on the hardmask layer, forming a photoresist layer on the silicon-containing thin layer, forming a photoresist pattern by exposing and developing the photoresist layer, exposing and developing the photoresist layer to form a photoresist pattern, selectively removing the silicon-containing thin layer and the hardmask layer using the photoresist pattern to expose a part of the material layer, and etching an exposed part of the material layer.

The hardmask composition may be applied using a spin-on coating method.

The hardmask layer may be heat-treated at about 100 to 500° C.

According to the embodiment of the present invention, the hardmask composition may satisfy chemical resistance, heat resistance and etch resistance while ensures dissolubility for a solvent, gap-fill characteristics, and planarization characteristics.

DETAILED DESCRIPTION

Exemplary embodiments of the present invention will hereinafter be described in detail. However, these embodiments are only exemplary and do not limit the present invention. As those skilled in the art would realize, the described embodiments may be modified in various different ways, all without departing from the spirit or scope of the present invention.

As used herein, when a definition is not otherwise provided, the term 'substituted' refers to one substituted with at least a substituent selected from a halogen (F, Br, Cl or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C20 heterocycloalkyl group, and a combination thereof, instead of hydrogen of a compound.

As used herein, when a definition is not otherwise provided, the prefix "hetero" refers to one including 1 to 3 heteroatoms selected from N, O, S, and P.

Hereinafter, a monomer for a hardmask composition according to one embodiment is described.

The monomer for a hardmask composition according to one embodiment may be represented by the following Chemical Formula 1.

[Chemical Formula 1]

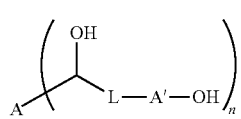

In Chemical Formula 1,

A and A' are the same or different and are each independently a substituted or unsubstituted aromatic group. A and A' may include at least one selected from the following Group 1.

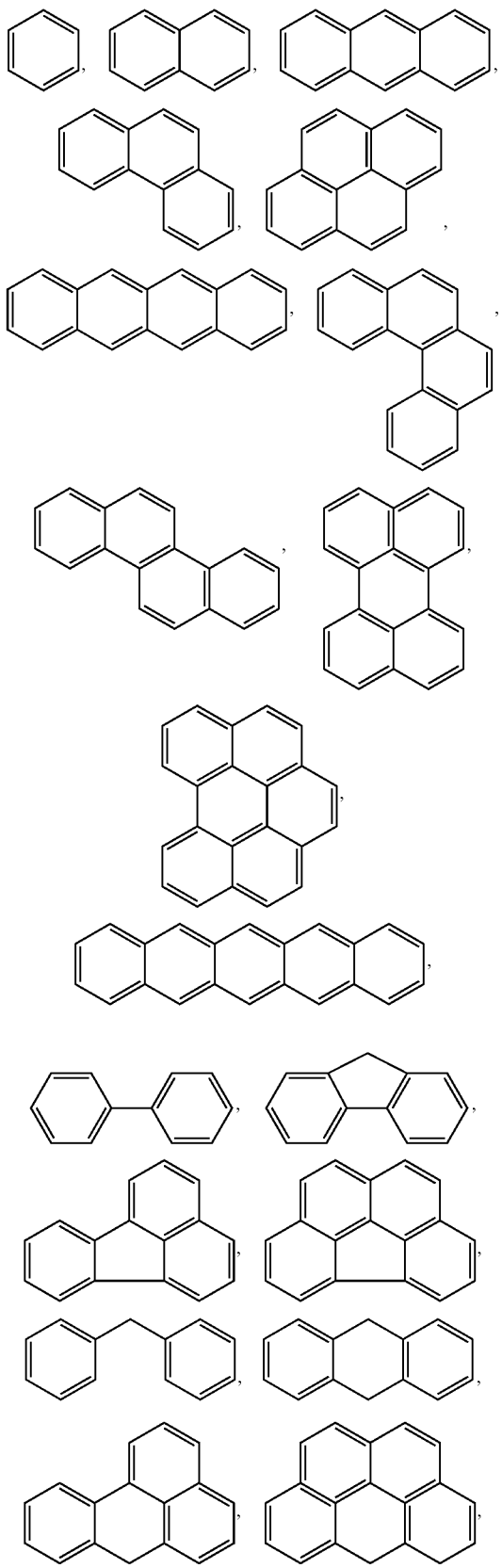

-continued

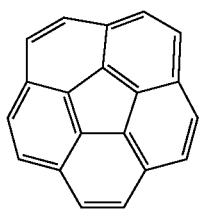 , 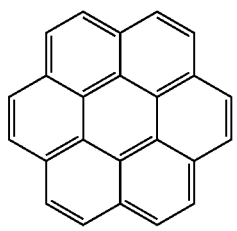

L is a linking group of a single bond or a substituted or unsubstituted C1 to C6 alkylene group, and n is an integer ranging from 1 to 5.

At least one of A and A' may include a substituted or unsubstituted polycyclic aromatic group.

The monomer may be, for example represented by the following Chemical Formula 1a, 1b, or 1c.

[Chemical Formula 1a]

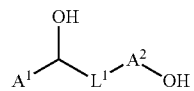

[Chemical Formula 1b]

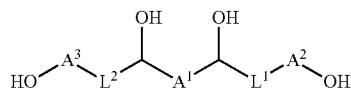

[Chemical Formula 1c]

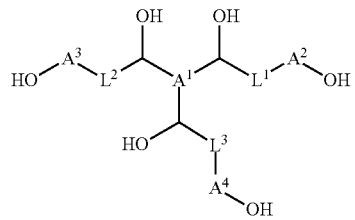

In Chemical Formula 1a, 1b, or 1c, $A^1$ to $A^4$ are each independently a substituted or unsubstituted benzene group, a naphthalene group, a pyrene group, a perylene group, a benzoperylene group, a coronene group, or a combination thereof.

$L^1$ to $L^3$ are each independently a single bond or a substituted or unsubstituted C1 to C6 alkylene group.

The monomer may be, for example represented by the following Chemical Formula 1aa, 1bb, 1cc, 1dd, or 1ee.

[Chemical Formula 1aa]

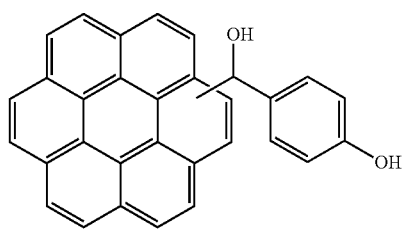

[Chemical Formula 1bb]

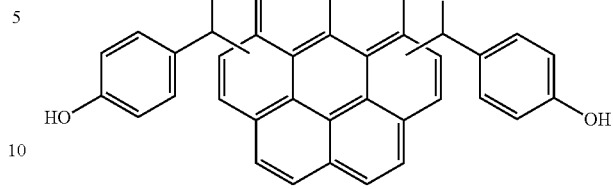

[Chemical Formula 1cc]

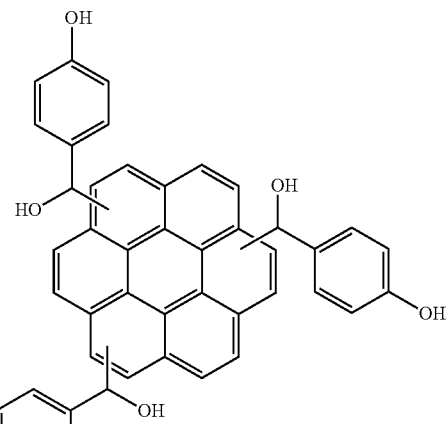

[Chemical Formula 1dd]

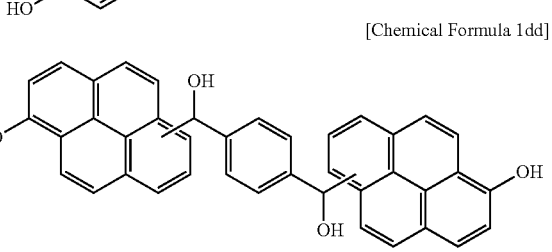

[Chemical Formula 1ee]

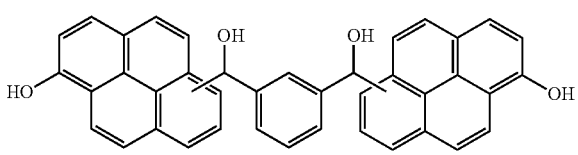

The monomer may have rigid characteristics by the plurality of aromatic rings.

Particularly, the monomer has a hydroxyl group and a hydroxyalkylene group, may be amplifying cross-linked due to the condensation reaction to provide excellent cross-linking characteristics.

Accordingly, the monomer may be cross-linked as a polymer having a high molecular weight within a short time during the heat treatment to provide excellent characteristics required for the hardmask layer such as excellent mechanical characteristics, heat resistance, chemical resistance, and etch resistance.

In addition, the monomer has a high dissolubility for a solvent by including a plurality of hydroxyl groups in the substituent, so as to provide as a solution and spin-coated to form a thin layer.

The monomer is spin-on coated on a lower layer having a predetermined pattern to provide excellent gap-fill characteristics to fill gaps between pattern, and planarization characteristics.

The monomer may have a molecular weight of about 200 to about 3,000. When the monomer has a molecular weight within the above range, solubility of the monomer having a high carbon content for a solvent is improved and an improved thin layer may be obtained through spin-on coating.

Hereinafter, a hardmask composition according to one embodiment is described.

The hardmask composition according to one embodiment includes the monomer and a solvent.

The monomer is the same as described above, and one kind of monomer may be used singularly and two or more kinds of monomers may be mixed.

The solvent may be anyone having sufficient dissolubility or dispersion for the monomer and may be, for example at least one selected from propyleneglycol, propyleneglycol diacetate, methoxy propanediol, diethyleneglycol, diethyleneglycol butylether, tri(ethyleneglycol)monomethylether, propyleneglycol monomethylether, propyleneglycol monomethylether acetate, cyclohexanone, ethyllactate, gamma-butyrolactone, methylpyrrolidone, and acetylacetone.

The monomer may be included in an amount of about 0.1 to about 30 wt % based on the total amount of the hardmask composition. When the monomer is included in the above range, a thickness of a coated thin layer may be obtained.

The hardmask composition may further include a surfactant.

The surfactant may include, for example, an alkylbenzene sulfonate salt, an alkyl pyridinium salt, polyethylene glycol, or a quaternary ammonium salt, but is not limited thereto.

The surfactant may be included in an amount of about 0.001 to 3 parts by weight based on 100 parts by weight of the hardmask composition. Within the amount range, the solubility and the cross-linking may be secured while not changing the optical properties of the hardmask composition.

Hereafter, a method for forming patterns by using the hardmask composition is described.

A method of forming a pattern according to one embodiment substrate includes providing a material layer on a substrate, applying a hardmask composition including the monomer and a solvent on the material layer, heat-treating the hardmask composition to provide a hardmask layer, forming a silicon-containing thin layer on the hardmask layer, forming a photoresist layer on the silicon-containing thin layer, forming a photoresist pattern by exposing and developing the photoresist layer, selectively removing the silicon-containing thin layer and the hardmask layer by using the photoresist pattern and exposing a part of the material layer, and etching the exposed part of the material layer.

The substrate may be, for example, a silicon wafer, a glass substrate, or a polymer substrate.

The material layer is a material to be finally patterned, for example a metal layer such as an aluminum layer and a copper layer, a semiconductor layer such as a silicon layer, or an insulation layer such as a silicon oxide layer and a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example about 100 Å to 10,000 Å.

The heat-treating the hardmask composition may be performed, for example about 100 to 500° C. for about 10 seconds to 10 minutes. During heat-treating, the monomer may cause a self cross-linking and/or mutual cross-linking reaction.

The silicon-containing thin layer may be made of, for example silicon nitride or silicon oxide.

A bottom anti-reflective coating (BARC) may be formed on the silicon-containing thin layer.

The exposure of the photoresist layer may be performed using for example ArF, KrF, or EUV. Also, after the exposure, heat-treating may be performed at about 100 to 500° C.

The etching process of the exposed part of the material layer may be performed through a dry etching process using an etching gas, and the etching gas may be, for example $CHF_3$, $CF_4$, $Cl_2$, $BCl_3$, and a mixed gas thereof.

The etched material layer may be formed in a plurality of pattern, and the plurality of pattern may be a metal pattern, a semiconductor pattern, an insulation pattern, and the like, for example diverse pattern of a semiconductor integrated circuit device.

Hereinafter, the present invention is illustrated in more detail with reference to examples. However, they are exemplary embodiments of the present invention and are not limiting.

Synthesis of Monomer

Synthesis Example 1

First Step

Friedel-Craft Acylation Reaction 50.0 g (0.166 mol) of coronene, 28.4 g (0.1666 mol) of 4-methoxybenzoylchloride, and 235 g of 1,2-dichloroethane were put in a flask, preparing a solution. Then, 22.2 g (0.166 mol) of aluminum chloride was slowly added to the solution at room temperature. The mixture was heated up to 60° C. and then, agitated for 8 hours. When the reaction was complete, methanol was added to the agitated solution. Then, a precipitate produced therein was filtrated, obtaining 4-methoxybenzoyl coronene.

Second Step

Demethylation 50.0 g (0.115 mol) of the 4-methoxybenzoyl coronene obtained in the first step, 58.2 g (0.288 mol) of 1-dodecanethiol, 19.4 g (0.345 mol) of potassium hydroxide, and 191 g of N,N-dimethylformamide was put in a flask, and the mixture was agitated for 120° C. for 8 hours. The agitated mixture was cooled down, neutralized with a 10% hydrogen chloride solution into about pH 7, and extracted with ethyl acetate, obtaining 4-hydroxybenzoyl coronene.

Third Step

Reduction Reaction 25.0 g (0.0595 mol) of the 4-hydroxybenzoyl coronene obtained in the second step and 145 g of tetrahydrofuran were put in a flask, preparing a solution. Then, 11.3 g (0.297 mol) of a sodium borohydride aqueous solution was slowly added to the solution, and the mixture was agitated at room temperature for 24 hours. When the reaction was complete, the agitated mixture was neutralized with a 10% hydrogen chloride solution into about pH 7 and extracted with ethyl acetate, obtaining a monomer represented by the following Chemical Formula 1aa.

[Chemical Formula 1aa]

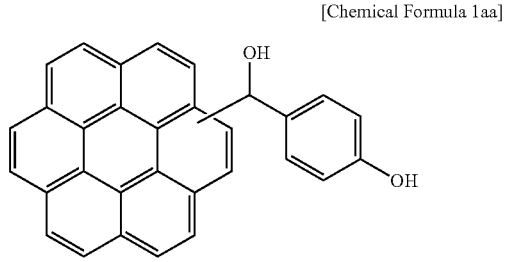

Synthesis Example 2

First Step

Friedel-Craft Acylation Reaction 50.0 g (0.166 mol) of coronene, 56.8 g (0.333 mol) of 4-methoxybenzoylchloride, and 353 g of 1,2-dichloroethane were put in a flask, preparing a solution. Then, 44.4 g (0.333 mol) of aluminum chloride was slowly added to the solution at room temperature, and the mixture was heated up to 60° C. and agitated for 8 hours. When the reaction was complete, methanol was added to the solution. Then, a precipitate produced therein was filtrated, obtaining double substituted 4-methoxybenzoyl coronene.

Second Step

Demethylation 50.0 g (0.880 mol) of the double substituted 4-methoxybenzoyl coronene obtained in the first step, 89.0 g (0.440 mol) of 1-dodecanethiol, 29.6 g (0.528 mol) of potassium hydroxide, and 253 g of N,N-dimethylformamide were put in a flask. The mixture was agitated at 120° C. for 8 hours. Then, the agitated mixture was cooled down, neutralized with a 10% hydrogen chloride solution into about pH 7, and extracted with ethyl acetate, obtaining double substituted 4-hydroxybenzoyl coronene.

Third Step

Reduction Reaction 25.0 g (0.0463 mol) of the double substituted 4-hydroxybenzoyl coronene obtained in the second step and 170 g of tetrahydrofuran were put in a flask, preparing a solution. Then, 17.5 g (0.463 mol) of a sodium borohydride aqueous solution was slowly added to the solution. The mixture was agitated at room temperature for 24 hours. When the reaction was complete, the agitated mixture was neutralized with a 10% hydrogen chloride solution into about pH 7 and extracted with ethyl acetate, obtaining a monomer represented by the following Chemical Formula 1bb.

[Chemical Formula 1bb]

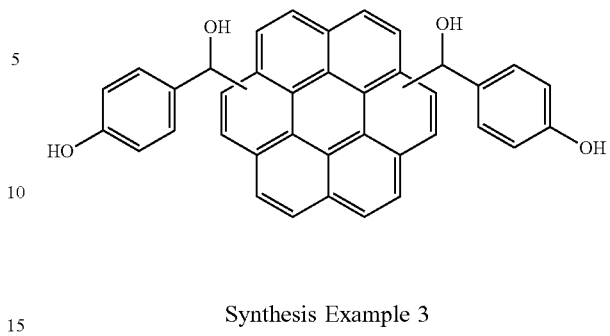

Synthesis Example 3

First Step

Friedel-Craft Acylation Reaction 50.0 g (0.166 mol) of coronene, 85.2 g (0.499 mol) of 4-methoxybenzoylchloride, and 471 g of 1,2-dichloroethane were put in a flask, preparing a solution. Then, 66.6 g (0.499 mol) of aluminum chloride was slowly added to the solution at room temperature. The mixture was heated up to 60° C. and agitated for 8 hours. When the reaction was complete, methanol was added to the solution. Then, a precipitate produced therein was filtrated triple substituted 4-methoxybenzoyl coronene.

Second Step

Demethylation 50.0 g (0.0712 mol) of the triple substituted 4-methoxybenzoyl coronene flask obtained in the first step, 108.0 g (0.534 mol) of 1-dodecanethiol, 35.9 g (0.640 mol) of potassium hydroxide, and 291 g of N,N-dimethylformamide were put in a flask. The mixture was agitated at 120° C. and agitated for 8 hours. Then, the agitated mixture was cooled down, neutralized with a 10% hydrogen chloride solution into about pH 7, and extracted with ethyl acetate, obtaining triple substituted 4-hydroxybenzoyl coronene.

Third Step

Reduction Reaction 25.0 g (0.0378 mol) of the triple substituted 4-hydroxybenzoyl coronene obtained in the second step and 186 g of tetrahydrofuran were put in a flask, preparing a solution. Then, 21.5 g (0.567 mol) of a sodium borohydride aqueous solution was slowly added to the solution. The mixture was agitated at room temperature for 24 hours. When the reaction was complete, the agitated mixture was neutralized into about pH 7 with a 10% hydrogen chloride solution, and extracted with ethyl acetate, obtaining a monomer represented by the following Chemical Formula 1cc.

[Chemical Formula 1cc]

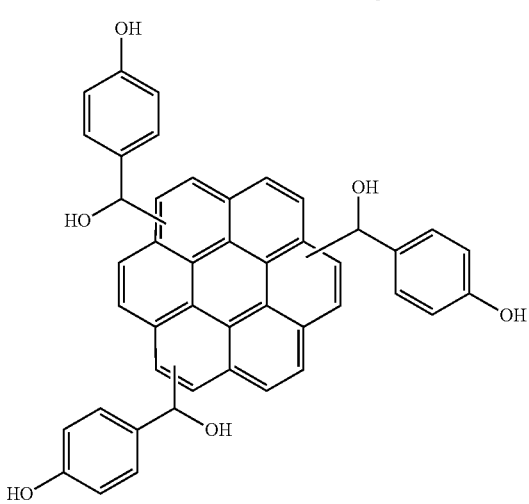

Synthesis Example 4

First Step

Friedel-Craft Acylation Reaction 20.6 g (0.101 mol) of terephthaloyl chloride, 47.0 g (0.203 mol) of 1-methoxypyrene, and 221 9 of 1,2-dichloroethane were put in a flask, preparing a solution. Then, 27 g (0.203 mol) of aluminum chloride was slowly added to the solution at room temperature. The mixture was heated up to 60° C. and agitated 10 for 8 hours. When the reaction was complete, methanol was added to the solution. Then, a precipitate produced therein was filtrated, obtaining bis(methoxypyrenyl carbonyl)benzene.

Second Step

Demethylation 53.5 g (0.0900 mol) of bis(methoxypyrenyl carbonyl)benzene obtained in the first step, 91.1 g (0.450 mol) of 1-dodecanethiol, 30.3 g (0.540 mol) of potassium hydroxide, and 262 g of N,N-dimethylformamide were put in a flask and then, agitated at 120° C. for 8 hours. Then, the agitated mixture was cooled down and neutralized into about pH 7 with a 5% hydrogen chloride solution. Then, a precipitate produced therein was filtrated, obtaining bis(hydroxypyrenyl carbonyl)benzene.

Third Step

Reduction Reaction 24.0 g (0.0424 mol) of bis(hydroxypyrenyl carbonyl)benzene obtained in the second step and 160 g of tetrahydrofuran were put in a flask, obtaining a solution. Then, 16.0 g (0.424 mol) of a sodium borohydride aqueous solution was slowly added to the solution, and the mixture was agitated at room temperature for 24 hours. When the reaction was complete, the agitated mixture was neutralized into about pH 7 with a 5% hydrogen chloride solution and extracted with ethyl acetate, obtaining a monomer represented by the following Chemical Formula 1dd.

[Chemical Formula 1dd]

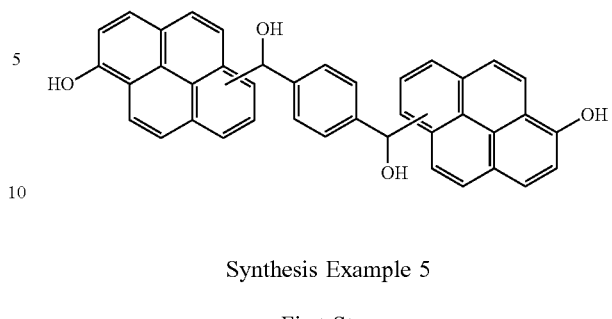

Synthesis Example 5

First Step

Friedel-Craft Acylation Reaction 20.0 g (0.0985 mol) of isophthaloyl chloride, 45.8 g (0.197 mol) of 1-methoxypyrene, and 215 g of 1,2-dichloroethane were put in a flask, preparing a solution. Then, 26.3 g (0.197 mol) of aluminum chloride was slowly added to 20 the solution at room temperature, and the mixture was heated up to 60° C. for 8 hours. When the reaction was complete, methanol was added to the agitated solution. Then, a precipitate produced therein was filtrated, obtaining bis(methoxypyrenyl carbonyl)benzene.

Second Step

Demethylation 50.0 g (0.0840 mol) of the bis(methoxypyrenyl carbonyl)benzene obtained in the first step, 85.1 g (0.420 mol) of 1-dodecanethiol, 28.3 g (0.504 mol) of potassium hydroxide, and 245 g of N,N-dimethylformamide were put in a flask and agitated at 120° C. for 8 hours. The agitated mixture was cooled down and neutralized into about pH 7 with a 5% hydrogen chloride solution. Then, a precipitate produced therein was filtrated, obtaining bis(hydroxypyrenyl carbonyl)benzene.

Third Step

Reduction Reaction 24.0 g (0.0424 mol) of the bis(hydroxypyrenyl carbonyl)benzene obtained in the second step and 160 g of tetrahydrofuran were put in a flask, preparing a solution. Then, 16.0 g (0.424 mol) of a sodium borohydride aqueous solution was slowly added to the solution, and the mixture was agitated at room temperature for 24 hours. When the reaction was complete, the agitated mixture was neutralized into about pH 7 with a 5% hydrogen chloride solution and extracted with ethyl acetate, obtaining a monomer represented by the following Chemical Formula 1ee.

[Chemical Formula 1ee]

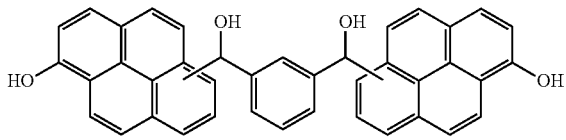

Comparative Synthesis Example 1

First Step

Friedel-Craft Acylation Reaction 50.0 g (0.166 mol) of coronene, 46.8 g (0.333 mol) of benzoylchloride, and 330 g of 1,2-dichloroethane were put in a flask, preparing a solution. Then, 44.4 g (0.333 mol) of aluminum chloride was slowly added to the solution at room temperature, and the mixture was heated up to 60° C. and agitated for 8 hours. When the reaction was complete, methanol was added to the solution. Then, a precipitate produced therein was filtrated, obtaining double substituted benzoyl coronene.

Second Step

Reduction Reaction 25.0 g (0.0492 mol) of the double substituted benzoyl coronene obtained in the first step and 174 g of tetrahydrofuran were put in a flask, preparing a solution. Then, 18.6 g (0.492 mol) of a sodium borohydride aqueous solution was slowly added to the solution, and the mixture was agitated at room temperature for 24 hours. When the reaction was complete, the agitated mixture was neutralized into about pH 7 with a 10% hydrogen chloride solution and extracted with ethyl acetate, obtaining a monomer represented by the following Chemical Formula 2.

[Chemical Formula 2]

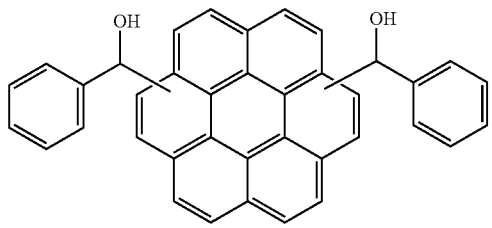

Comparative Synthesis Example 2

First Step

Friedel-Craft Acylation Reaction 13.9 g (0.0989 mol) of benzoyl chloride, 10.0 g (0.0495 mol) of pyrene, and 87 g of 1,2-dichloroethane were put in a flask. Then, 13.2 g (0.0989 mol) of aluminum chloride was slowly added to the solution at room temperature, and the mixture was heated up to 60° C. and agitated for 8 hours. When the reaction was complete, methanol was added to the agitated mixture. Then, a precipitate produced therein was filtrated, obtaining dibenzoyl pyrene.

Second Step

Reduction Reaction 5.00 g (0.0122 mol) of dibenzoyl pyrene and 57 g of tetrahydrofuran were put in a flask. Then, 4.60 g (0.122 mol) of a sodium borohydride aqueous solution was slowly added to the solution. The mixture was agitated at room temperature for 24 hours. When the reaction was complete, the agitated mixture was neutralized into about pH 7 with a 5% hydrogen chloride solution and extracted with ethylacetate, obtaining a monomer represented by the following Chemical Formula 3.

[Chemical Formula 3]

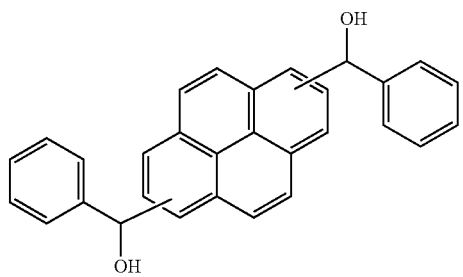

Comparative Synthesis Example 3

8.75 g (0.05 mol) of α,α'-dichloro-p-xylene, 26.66 g of aluminum chloride, and 200 g of γ-butyrolactone were put in a flask. Then, a solution prepared by dissolving 35.03 g (0.10 mol) of 4,4'-(9-fluorenylidene)diphenol in 200 g of γ-butyrolactone was slowly added to the solution. The mixture was agitated at 120° C. for 12 hours. After the polymerization, acid was removed from the agitated mixture using water, and the remnant was concentrated. Then, a polymerized product was diluted using methylamylketone and methanol, and a solution of methylamylketone/methanol mixed in a weight ratio of 4/1 and having 15 wt % of a concentration was added thereto to adjust its concentration. This solution was put in a separatory funnel, and n-heptane was added thereto to remove a monomer and a low molecular sieve, obtaining a polymer represented by the following Chemical Formula 4.

[Chemical Formula 4]

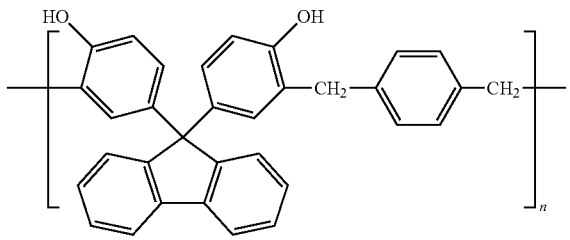

The polymer had a weight average molecular weight of 12,000 and dispersity of 2.04.

Preparation of Hardmask Composition

Example 1

A hardmask composition was prepared by dissolving the monomer according to Synthesis Example 1 in a mixed solvent prepared by mixing propyleneglycol monomethylether acetate (PGMEA) and cyclohexanone (7:3 (v/v)) and filtering the mixture. The monomer may be included in a weight of 10.0 wt % or 13.0 wt % based on the total weight of the hardmask composition depending on a desired thickness.

Example 2

A hardmask composition was prepared in accordance with the same procedure as Example 1, except that the monomer obtained from Synthesis Example 2 was used instead of the monomer obtained from Synthesis Example 1.

Example 3

A hardmask composition was prepared in accordance with the same procedure as Example 1, except that the monomer obtained from Synthesis Example 3 was used instead of the monomer obtained from Synthesis Example 1.

Example 4

A hardmask composition was prepared in accordance with the same procedure as Example 1, except that the monomer obtained from Synthesis Example 4 was used instead of the monomer obtained from Synthesis Example 1.

Example 5

A hardmask composition was prepared in accordance with the same procedure as Example 1, except that the monomer obtained from Synthesis Example 5 was used instead of the monomer obtained from Synthesis Example 1.

Comparative Example 1

A hardmask composition was prepared in accordance with the same procedure as Example 1, except that the monomer obtained from Comparative Synthesis Example 1 was used instead of the monomer obtained from Synthesis Example 1.

Comparative Example 2

A hardmask composition was prepared in accordance with the same procedure as Example 1, except that the monomer obtained from Comparative Synthesis Example 2 was used instead of the monomer obtained from Synthesis Example 1.

Comparative Example 3

A hardmask composition was prepared in accordance with the same procedure as Example 1, except that the monomer obtained from Comparative Synthesis Example 3 was used instead of the monomer obtained from Synthesis Example 1.

Evaluation 1

Chemical Resistance

Each hardmask composition including 10.0 wt % of the monomer according to Examples 1 to 5 and Comparative Examples 1 and 2 was spin-on coated on a silicon wafer and then heat-treated on a hot plate at 240° C. for 1 minute to provide a thin layer. Initial thicknesses of the thin layers were measured by a thin layer thickness gauge manufactured by K-MAC.

Then, the thin layer was dipped in a mixed solvent of ethyl 3-ethoxypropinonate (EEP) and ethyl lactate (EL) (7:3 (v/v)) as a peeling solution for one minute and measured regarding thickness.

The results are shown in Table 1.

TABLE 1

| | Initial thickness of thin layer (Å) | Thickness of thin layer after dipping (Å) | Decrease ratio of thickness of thin layer (%) |
|---|---|---|---|
| Example 1 | 2,342 | 2,125 | −9.27 |
| Example 2 | 2,733 | 2,725 | −0.29 |
| Example 3 | 2,940 | 2,937 | −0.10 |
| Example 4 | 2,663 | 2,660 | −0.11 |
| Example 5 | 2,996 | 2,972 | −0.80 |
| Comparative Example 1 | 2,042 | 342 | −83.3 |
| Comparative Example 2 | 2,490 | 123 | −95.1 |

Referring to Table 1, each thin layer formed of the hardmask composition according to Examples 1 to 5 had a less thickness decrease rate than ones formed of the hardmask compositions according to Comparative Examples 1 and 2.

Accordingly, the hardmask compositions according to Examples 1 to 5 were sufficiently cross-linked through a heat treatment at a relatively low temperature of 240° C. compared with the ones according to Comparative Examples 1 and 2 and formed a thin layer having high chemical resistance.

Evaluation 2

Heat Resistance

Each hardmask composition including 10.0 wt % of the monomer according to Examples 1 to 5 and Comparative Examples 1 and 2 was spin-on coated on a silicon wafer and then heat-treated on a hot plate at 240° C. for 1 minute to provide a thin layer. Thicknesses of the thin layers were measured by a thin layer thickness gauge manufactured by K-MAC.

Then, the thin layer was heat-treated again at 400° C. for 2 minutes and measured regarding thickness.

The results are shown in Table 2.

TABLE 2

| | Thickness of thin layer (Å) after 240° C. heat treating | Thickness of thin layer (Å) after 400° C. heat treating | Decrease ratio of thickness of thin layer (%) |
|---|---|---|---|
| Example 1 | 2,338 | 2,050 | −12.31 |
| Example 2 | 2,736 | 2,518 | −7.97 |
| Example 3 | 2,948 | 2,813 | −4.58 |
| Example 4 | 2,713 | 2,408 | −11.2 |
| Example 5 | 3,053 | 2,767 | −9.37 |
| Comparative Example 1 | 2,045 | 1,348 | −34.08 |
| Comparative Example 2 | 2,479 | 310 | −87.5 |

Referring to Table 2, each thin layer formed of the hardmask compositions according to Examples 1 to 5 had a less thickness decrease rate than the ones formed of the hardmask compositions according to Comparative Examples 1 and 2 during the heat treatment at 400° C.

Accordingly, the hardmask compositions according to Examples 1 to 5 were highly cross-linked compared with the ones according to Comparative Examples 1 and 2 and high heat resistance during the heat treatment at a high temperature of 400° C.

Evaluation 3-1

Etching Resistance (1)

The hardmask compositions including 13 wt % of the monomer according to Examples 1 to 3 and Comparative Example 1 were spin-on coated on a silicon wafer and then heat-treated on a hot plate at 240° C. for 1 minute to provide a thin layer. The thin layers were measured regarding thicknesses by a thin layer thickness gauge manufactured by K-MAC.

Then, the thin layers were dry-etched using a $N_2/O_2$ mixed gas for 60 seconds and measured regarding thickness, and its etching rate was calculated from the thickness measurements.

The results are shown in Table 3.

TABLE 3

|  | Initial thickness of thin layer (Å) | Thickness of thin layer (Å) after etching | etching rate (Å/s) |
|---|---|---|---|
| Example 1 | 4,427 | 3,012 | 23.6 |
| Example 2 | 4,532 | 3,117 | 23.6 |
| Example 3 | 4,708 | 3,322 | 23.1 |
| Comparative Example 1 | 4,112 | 2,535 | 26.3 |

* etching rate (bulk etching rate, BER): (Initial thickness of thin layer − thickness of thin layer after etching)/etching time (second)

Referring to Table 3, the thin layers formed of the hardmask compositions according to Examples 1 to 3 had a lower etching rate than the ones formed of the hardmask compositions according to Comparative Example 1.

Accordingly, the thin layers formed of the hardmask compositions according to Examples 1 to 3 were highly cross-linked compared with the one formed of the hardmask composition according to Comparative Example 1 had high etching resistance.

Evaluation 3-2

Etching Resistance 2

Each hardmask composition including 13 wt % of the monomer according to Examples 4 and 5 and Comparative Examples 2 and 3 was spin-on coated on a silicon wafer and then heat-treated on a hot plate at 240° C. for 1 minute to provide a thin layer. Thicknesses of the thin layers were measured by a thin layer thickness gauge manufactured by K-MAC.

Then, the thin layers were dry-etched for 60 seconds using a $N_2/O_2$ mixed gas and measured regarding thickness. In addition, the thin layers were dry-etched for 100 seconds using a CFx mixed gas and measured regarding thickness.

The results are shown in Table 4.

TABLE 4

|  | $N_2/O_2$ | | | CFx | | |
|---|---|---|---|---|---|---|
|  | Initial thickness of thin layer (Å) | Thickness of thin layer (Å) after etching | Etching rate (Å/s) | Initial thickness of thin layer (Å) | Thickness of thin layer (Å) after etching | Etching rate (Å/s) |
| Example 4 | 4,093 | 2,765 | 22.1 | 4,090 | 1,540 | 25.5 |
| Example 5 | 4,048 | 2,704 | 22.4 | 4,056 | 1,496 | 25.6 |
| Comparative Example 2 | 3,503 | 1,673 | 30.5 | 3,518 | 418 | 31.0 |
| Comparative Example 3 | 4,081 | 2,570 | 25.2 | 4,061 | 1,276 | 27.9 |

*etching rate (bulk etching rate, BER): (Thickness of initial thickness of thin layer − Thickness of thin layer after etching)/etching time (seconds)

Referring to Table 4, the thin layers formed of the hardmask compositions according to Examples 4 and 5 had a lower etching rate than the ones formed of the hardmask compositions according to Comparative Examples 2 and 3.

Accordingly, the thin layers formed of the hardmask compositions according to Examples 4 and 5 had higher etching resistance than the ones formed of the hardmask compositions according to Comparative Examples 2 and 3.

Evaluation 4

Formation of Pattern

A 3,000 Å-thick silicon oxide $SiO_2$ layer was formed on a silicon wafer in a chemical vapor deposition method. Next, the hardmask compositions including 13.0 wt % of a monomer or a polymer according to Examples 1 to 5 and Comparative Examples 1 to 3 were respectively coated on the silicon oxide layer in a spin-on coating method and heat-treated on a hot plate at 240° C. for 1 minute, forming a hardmask layer. Then, a nitride silicon (SiN) layer was formed on the hardmask layer in a chemical vapor deposition method. On the nitride silicon (SiN) layer, a photoresist for KrF was coated, heat-treated at 110° C. for 60 seconds, exposed to a light using ASML (XT: 1400, NA 0.93) using an exposure equipment, and developed with tetramethylammonium hydroxide (a 2.38 wt % TMAH aqueous solution). The patterned photoresist as a mask and a $CHF_3/CF_4$ mixed gas were used to dry-etch the silicon nitride layer. The patterned silicon nitride layer as a mask and a $N_2/O_2$ mixed gas were used to dry-etch a hardmask layer. The patterned hardmask layer as a mask and a $CHF_3/CF_4$ mixed gas were used to dry-etch a silicon oxide layer, and an organic material remaining after the dry etching was all removed using $O_2$ gas.

The hardmask layer and the silicon oxide layer were examined about the cross sections using a scanning electronic microscope (SEM). The results are shown in Table 5.

TABLE 5

| | Pattern profile of hardmask layer | Pattern profile of silicon oxide layer |
|---|---|---|
| Example 1 | vertical shape | vertical shape |
| Example 2 | vertical shape | vertical shape |
| Example 3 | vertical shape | vertical shape |
| Example 4 | vertical shape | vertical shape |
| Example 5 | vertical shape | vertical shape |
| Comparative Example 1 | tapered shape | tapered shape |
| Comparative Example 2 | tapered shape | tapered shape |
| Comparative Example 3 | tapered shape | tapered shape |

Referring to Table 5, the hardmask layers formed of the hardmask compositions according to Examples 1 to 5 and the silicon oxide layers beneath them were all vertically patterned, while the hardmask layers formed of the hardmask compositions according to Comparative Examples 1 to 3 were not vertically patterned but tapered.

Accordingly, the hardmask layers formed of the hardmask compositions according to Examples 1 to 5 had excellent etching resistance and were well patterned compared with the ones formed of the hardmask compositions according to Comparative Examples 1 to 3, and thus, the underlayer beneath the hardmask layers were well patterned.

Evaluation 5

Gap-Filling and Planarization Characteristics

The hardmask composition including 13.0 wt % of a monomer or a polymer according to Examples 4 and 5 and Comparative Examples 2 and 3 were spin-on coated on a patterned silicon wafer and heat-treated at 240° C. for 60 seconds and then, examined regarding gap-filling and planarization characteristics using a FE-SEM equipment.

The gap-filling characteristics were determined by observing the cross sectional surface of pattern using a scanning electron microscope (SEM) and counting void, and the planarization characteristics were calculated according to the following Equation 1 after measuring the thickness of hardmask layer from the image of pattern cross-sectional surface observed from SEM. Since the planarization characteristics are more excellent, as a difference between $h_1$ and $h_2$ is smaller, the planarization characteristics are better as the number is smaller.

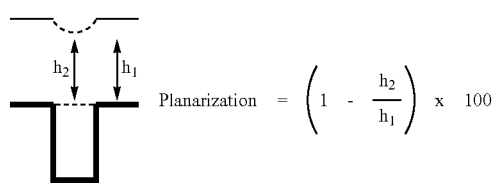

$$\text{Planarization} = \left(1 - \frac{h_2}{h_1}\right) \times 100 \quad \text{[Equation 1]}$$

The results are shown in Table 6.

TABLE 6

| | Planarization characteristic | Gap-filling characteristic |
|---|---|---|
| Example 4 | 10.3 | No void |
| Example 5 | 10.8 | No void |
| Comparative Example 2 | 17.0 | Void |
| Comparative Example 3 | 128.0 | No void |

Referring to Table 6, the case of using the hardmask compositions according to Examples 4 and 5 had better planarization and no void than the case of using hardmask compositions according to Comparative Examples 2 and 3, so it is understood that had excellent gap-fill characteristics.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A monomer for a hardmask composition represented by the following Chemical Formula 1:

[Chemical Formula 1]

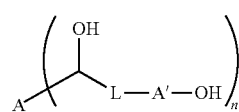

wherein, in Chemical Formula 1,

A and A' are the same or different and are each independently a substituted or unsubstituted aromatic group selected from the following Group 1, L is a single bond or a substituted or unsubstituted C1 to C6 alkylene group, and n is an integer ranging from 2 to 5, such that A has from 2 to 5 of the group

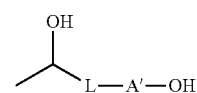

bonded thereto

[Group 1]

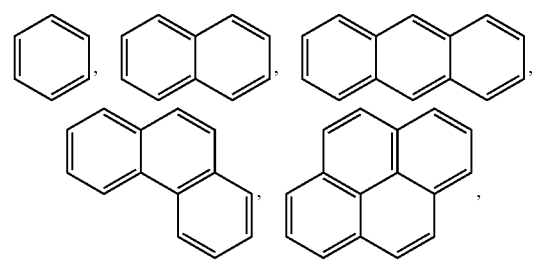

-continued

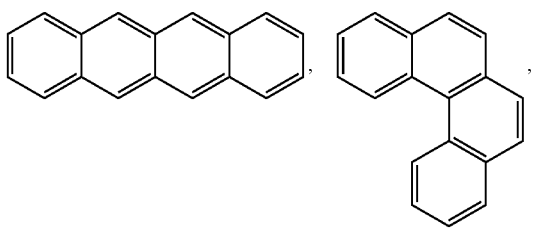

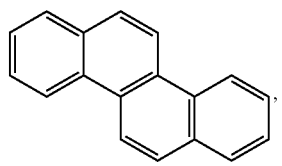

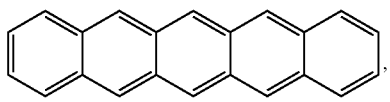

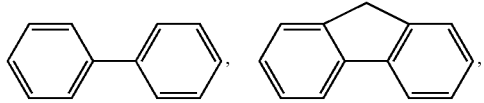

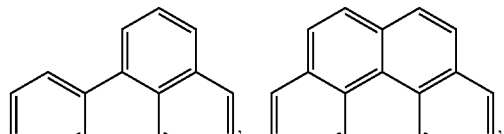

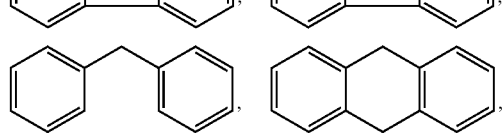

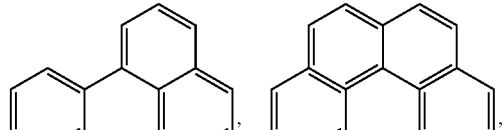

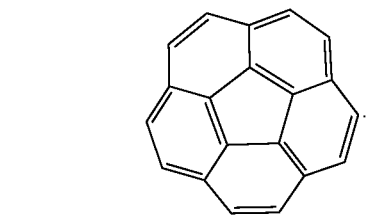

2. The monomer for a hardmask composition of claim 1, wherein at least one of A and A' comprises a substituted or unsubstituted polycyclic aromatic group.

3. The monomer for a hardmask composition of claim 1, wherein the monomer is represented by the following Chemical Formula 1b or 1c:

[Chemical Formula 1b]

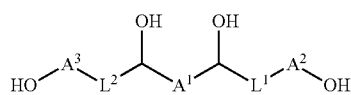

[Chemical Formula 1c]

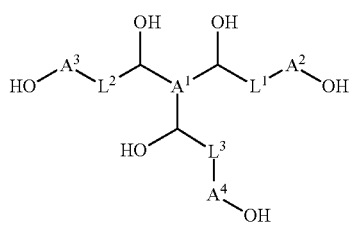

wherein, in Chemical Formula 1b and 1c, $A^1$ to $A^4$ are each independently a substituted or unsubstituted benzene group, a substituted or unsubstituted naphthalene group, a substituted or unsubstituted pyrene group, or a combination thereof, and $L^1$ to $L^3$ are each independently a single bond or a substituted or unsubstituted C1 to C6 alkylene group.

4. The monomer for a hardmask composition of claim 3, wherein the monomer is represented by the following Chemical Formula 1dd or 1ee:

[Chemical Formula 1dd]

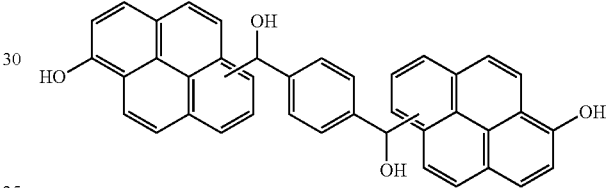

[Chemical Formula 1ee]

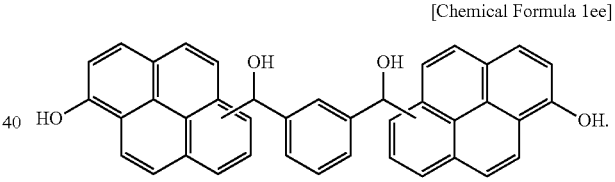

5. The monomer for a hardmask composition of claim 1, wherein the monomer has a molecular weight of about 200 to 3,000.

6. The monomer for a hardmask composition of claim 1, wherein A is a substituted or unsubstituted aromatic group selected from the following Group 1, provided that, when A is substituted, the substituent of A does not include a hydroxyl group,

[Group 1]

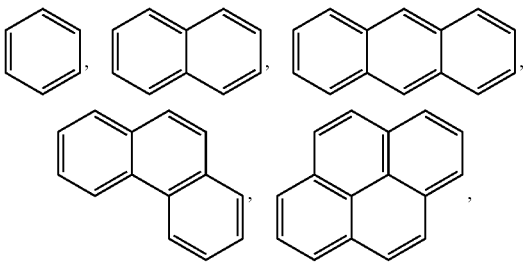

-continued

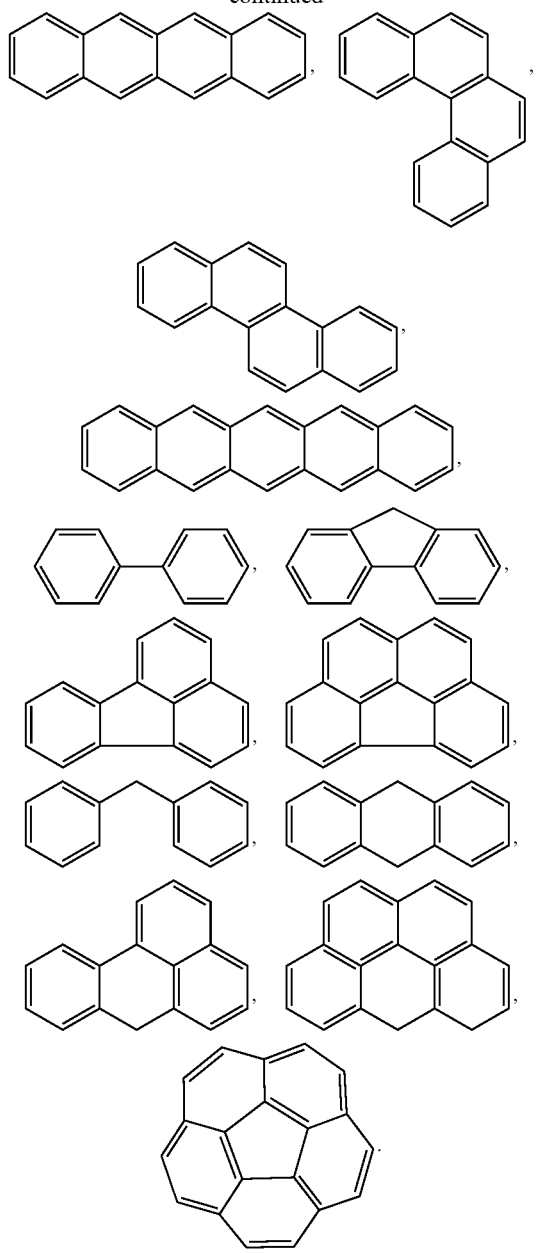

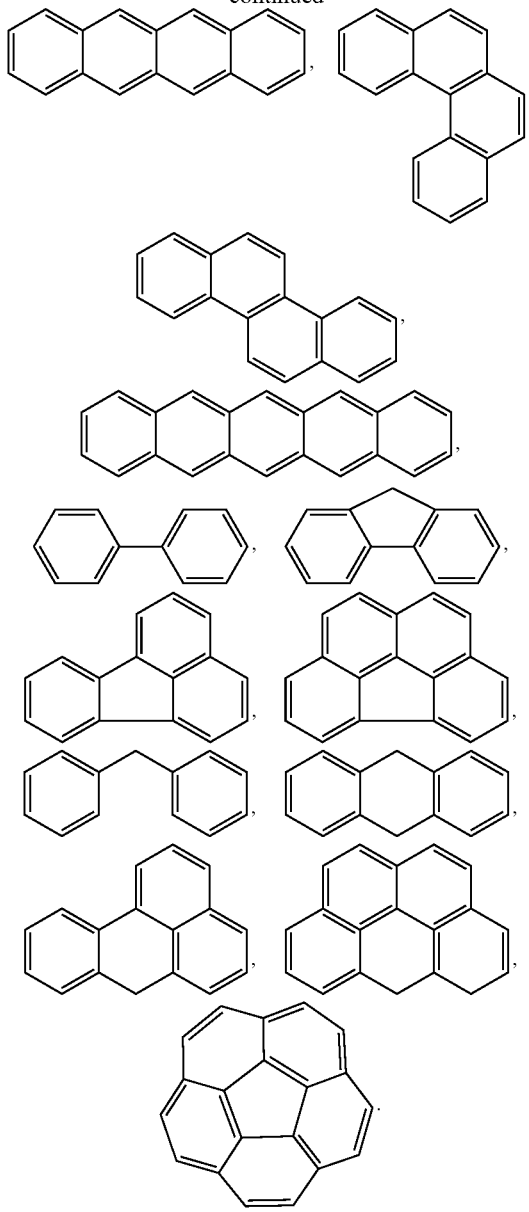

7. The monomer for a hardmask composition of claim 1, wherein A is an unsubstituted aromatic group selected from the following Group 1,

[Group 1]

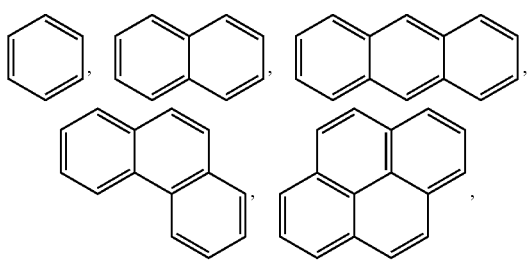

8. A hardmask composition, comprising the monomer of claim 1, and
 a solvent.

9. The hardmask composition of claim 8, wherein the monomer is included in an amount of about 0.1 to 30 wt % based on the total amount of the hardmask composition.

10. A method of forming a pattern, comprising:
 providing a material layer on a substrate,
 applying the hardmask composition according to claim 8 on the material layer,
 heat-treating the hardmask composition to provide a hardmask layer,
 forming a silicon-containing thin layer on the hardmask layer,
 forming a photoresist layer on the silicon-containing thin layer,
 forming a photoresist pattern by exposing and developing the photoresist layer, selectively removing the silicon-containing thin layer and the hardmask layer using the photoresist pattern to expose a part of the material layer, and etching an exposed part of the material layer.

11. The method of claim 10, wherein the hardmask composition is applied using a spin-on coating method.

12. The method of claim 10, wherein, in the heat-treating of the hardmask composition to provide the hardmask layer, the hardmask composition is heat-treated at about 100 to 500° C.

* * * * *